US012396818B2

(12) United States Patent
Ybarra et al.

(10) Patent No.: US 12,396,818 B2
(45) Date of Patent: Aug. 26, 2025

(54) FRICTION CREATING SURGICAL GLOVE

(71) Applicants: Daniel Joseph Ybarra, Pasadena, CA (US); Mark Richard Currie, Northridge, CA (US)

(72) Inventors: Daniel Joseph Ybarra, Pasadena, CA (US); Mark Richard Currie, Northridge, CA (US)

( * ) Notice: Subject to any disclaimer, the term of this patent is extended or adjusted under 35 U.S.C. 154(b) by 0 days.

(21) Appl. No.: 18/406,118

(22) Filed: Jan. 6, 2024

(65) Prior Publication Data
US 2025/0025253 A1    Jan. 23, 2025

Related U.S. Application Data

(60) Provisional application No. 63/514,296, filed on Jul. 18, 2023.

(51) Int. Cl.
*A41D 19/00* (2006.01)
*A41D 19/015* (2006.01)
*A61B 42/10* (2016.01)

(52) U.S. Cl.
CPC ............ *A61B 42/10* (2016.02); *A41D 19/001* (2013.01); *A41D 19/01558* (2013.01); *A41D 2500/00* (2013.01)

(58) Field of Classification Search
CPC .... A41D 19/002; A41D 19/001; A61B 42/00; A61B 42/10
See application file for complete search history.

(56) References Cited

U.S. PATENT DOCUMENTS

| 4,095,292 | A | * | 6/1978 | Klein | A41D 19/0006 2/164 |
| 4,197,592 | A | * | 4/1980 | Klein | A41D 19/0006 2/164 |
| 4,881,277 | A | * | 11/1989 | Hogle | A61B 42/00 2/161.7 |
| 10,251,435 | B1 | * | 4/2019 | Chou | A41D 19/0003 |
| 10,918,145 | B1 | * | 2/2021 | Mitchell | A41D 19/0082 |
| 2003/0010939 | A1 | * | 1/2003 | DeMeo | G21F 3/02 250/516.1 |
| 2004/0098786 | A1 | * | 5/2004 | Hottner | A41D 19/001 2/161.6 |
| 2006/0212990 | A1 | * | 9/2006 | Mattesky | A41D 19/0006 2/161.6 |
| 2008/0034466 | A1 | * | 2/2008 | Zicarelli | A41D 19/001 2/167 |
| 2009/0126074 | A1 | * | 5/2009 | Mattesky | A41D 19/01523 2/167 |
| 2013/0139294 | A1 | * | 6/2013 | Zetune | A61B 42/00 2/163 |
| 2013/0253462 | A1 | * | 9/2013 | Robson | A61F 13/104 604/385.03 |
| 2016/0186364 | A1 | * | 6/2016 | Rodrigues | D01D 5/36 442/361 |

(Continued)

FOREIGN PATENT DOCUMENTS

CA          2535309 A1 *  8/2007   .......... A41D 19/002

*Primary Examiner* — Jillian K Pierorazio

(57) ABSTRACT

A friction creating surgical glove system includes a cotton mesh superficial glove having a palmar portion, a thumb portion, a first finger portion, a second finger portion, a third finger portion, and a fourth finger portion, and a gauze pocket coupled to the cotton mesh superficial glove configured to house a radio-opaque liner.

20 Claims, 7 Drawing Sheets

(56) References Cited

U.S. PATENT DOCUMENTS

| | | | | |
|---|---|---|---|---|
| 2017/0027256 A1* | 2/2017 | Williams | ............... | A41D 27/02 |
| 2017/0095017 A1* | 4/2017 | Mirkarimi | .............. | A61B 46/10 |
| 2017/0318935 A1* | 11/2017 | Guirette | ............. | A45D 40/0087 |
| 2018/0344429 A1* | 12/2018 | Stewart | ................... | A61B 90/36 |
| 2019/0301675 A1* | 10/2019 | Rickey | ..................... | H04B 5/79 |
| 2021/0100217 A1* | 4/2021 | Mesiti | ....................... | B32B 3/08 |
| 2021/0219638 A1* | 7/2021 | Kessler | ..................... | A41F 1/06 |
| 2023/0337770 A1* | 10/2023 | Smid | ................... | A41D 19/001 |

\* cited by examiner

FRICTION CREATING SURGICAL GLOVE

CROSS REFERENCE TO RELATED APPLICATION

This application claims the benefit of U.S. Provisional Application Ser. No. 63/514,296, filed Jul. 18, 2023, the entirety of which is incorporated by reference herein.

BACKGROUND OF THE INVENTION

Technical Field

Aspects of embodiments of the present disclosure relate to the field personal protective equipment (PPE) for use within the medical context. More specifically, aspects of embodiments of the present disclosure are directed to friction creating surgical gloves that may provide increased friction during medical procedures where the surgical gloves may be exposed to various bodily fluids or smooth organs.

Problems That are to be Solved by the Invention

The use of personal protective equipment (PPE) during a medical procedure is a well-established standard of care. However, for some medical procedures such as surgical procedures or the delivery of a baby, there may be issues with the grip available to medical practitioners wearing traditional surgical gloves once they are exposed to bodily fluids like blood. Traditional surgical gloves, made from latex, nitrile, or other elastomeric compounds may become slippery when their surface is covered in blood or other bodily fluids. Currently available methods for addressing this issue, such as textured glove surfaces or the use of high coefficient-of-friction materials/coatings, come with significant drawbacks to the tactile attributes of such gloves, like the ability to feel fine textures through the glove and precisely control held objects, and increases to the cost of production. Additionally, due to these drawbacks, increased surgical time may be required to offer appropriate care during the operation increasing costs to the hospital and surgical team. Therefore, there is a need for a cost efficient surgical glove that can provide increased friction, and thereby increased grip, while wet with bodily fluids that does not hinder the tactile attributes that practitioners require for delicate surgical/medical procedures.

Means for Solving the Problem

As described above, there is a need for a cost efficient surgical glove that may provide increased friction while wet/damp with bodily fluids that does not limit or impair the tactile attributes required for delicate procedures. Some aspects of embodiments of the present disclosure are thus directed to surgical gloves that may increase friction by providing a superficial sterile cotton mesh layer that provides increased friction while wet. In some embodiments, the superficial cotton mesh layer may be used in conjunction with an elastomeric inner glove. Aspects of embodiments of the present disclosure may also be directed to removing portions of the superficial cotton mesh layer to allow for customization by practitioners to find their own balance between increased friction and the effects on the tactile attributes of the surgical gloves such as feel for fine textures and precise control of held objects.

Effect of the Invention

Some embodiments of the present disclosure may provide a surgical glove that features increased friction while wet with bodily fluids that does not overly limit or reduce the tactile attributes of the surgical glove available to a practitioner while wearing the surgical glove. Additionally, some embodiments of the present disclosure may provide practitioners with a customizable option for adapting a friction creating surgical glove to their specific needs. Some embodiments of the present disclosure may also offer a cost effective solution for providing a friction creating surgical glove that eliminates the need for the more costly production and use of texturized elastomeric gloves. Some such embodiments may offer additional cost saving benefits by allowing for the modular replacement of portions of the friction creating surgical glove that have become worn out during a procedure rather than replacing all of the surgical glove each time.

SUMMARY OF THE INVENTION

One or more embodiments of the present disclosure may be directed to a friction creating surgical glove.

A friction creating surgical glove system includes a cotton mesh superficial glove having a palmar portion, a thumb portion, a first finger portion, a second finger portion, a third finger portion, and a fourth finger portion, and a gauze pocket coupled to the cotton mesh superficial glove configured to house a radio-opaque liner.

The friction creating glove system may include an elastomeric inner glove configured to couple to the cotton mesh superficial glove.

The friction creating glove system may have the cotton mesh superficial glove further include sterilized medical grade, natural cellulose fiber, cotton.

The friction creating glove system may have the sterilized medical grade, natural cellulose fiber, cotton have a 24×20 mesh size.

The friction creating glove system may have the cotton mesh superficial glove further include a backhand portion.

The friction creating glove system may have the cotton mesh superficial glove form a continuous outer layer including the palmar portion, the backhand portion, the thumb portion, the first finger portion, the second finger portion, the third finger portion, and the fourth finger portion.

The friction creating glove system may have each of the first finger portion, the second finger portion, the third finger portion, and the fourth finger portion be configured having removeable fingertip portions.

The friction creating glove system may have the thumb portion be configured having a removeable thumb tip portion.

The friction creating glove system may have the radio-opaque liner include an RFID tag.

A friction creating surgical glove apparatus includes a cotton mesh superficial glove having a palmar portion, a thumb portion, and a finger portion, a gauze pocket coupled to the cotton mesh superficial glove configured to house a radio-opaque liner, and an elastomeric inner glove.

The friction creating surgical glove apparatus may have the cotton mesh superficial glove further include sterilized medical grade, natural cellulose fiber, cotton.

The friction creating surgical glove apparatus may have the sterilized medical grade, natural cellulose fiber, cotton have a 24×20 mesh size.

The friction creating surgical glove apparatus may have the finger portion include a distal tip that is severable from a proximal portion of the finger portion.

The friction creating surgical glove apparatus may have the thumb portion include a distal thumb tip that is severable from a proximal thumb portion of the thumb portion.

The friction creating surgical glove apparatus may have the radio-opaque liner include an RFID tag.

The friction creating surgical glove apparatus may have the radio-opaque liner include a liner material containing at least 55% barium sulfate.

The friction creating surgical glove apparatus may have the cotton mesh superficial glove be bonded to the elastomeric inner glove along a binding portion of the elastomeric inner glove.

A method for donning a friction creating surgical glove includes donning, by a user, an elastomeric inner glove, selecting, by the user, one or more fingertip portions of a cotton mesh superficial glove for removal, severing, by the user, the selected one or more fingertip portions of the cotton mesh superficial glove, and stretching, by the user, the cotton mesh superficial glove over the elastomeric inner glove thereby forming the friction creating surgical glove.

The method for donning a friction creating surgical glove may have the cotton mesh superficial glove include sterilized medical grade, natural cellulose fiber, cotton.

The method for donning a friction creating surgical glove may further include presenting, by the user, an RFID tag coupled to the friction creating surgical glove to an RF receiver.

BRIEF DESCRIPTION

The features and advantages of embodiments of the present disclosure will become more apparent by reference to the following detailed description when considered in conjunction with the following drawings. In the drawings, like reference numerals are used throughout the figures to reference like features and components. The figures are not necessarily drawn to scale.

DETAILED DESCRIPTION

Figure 1:
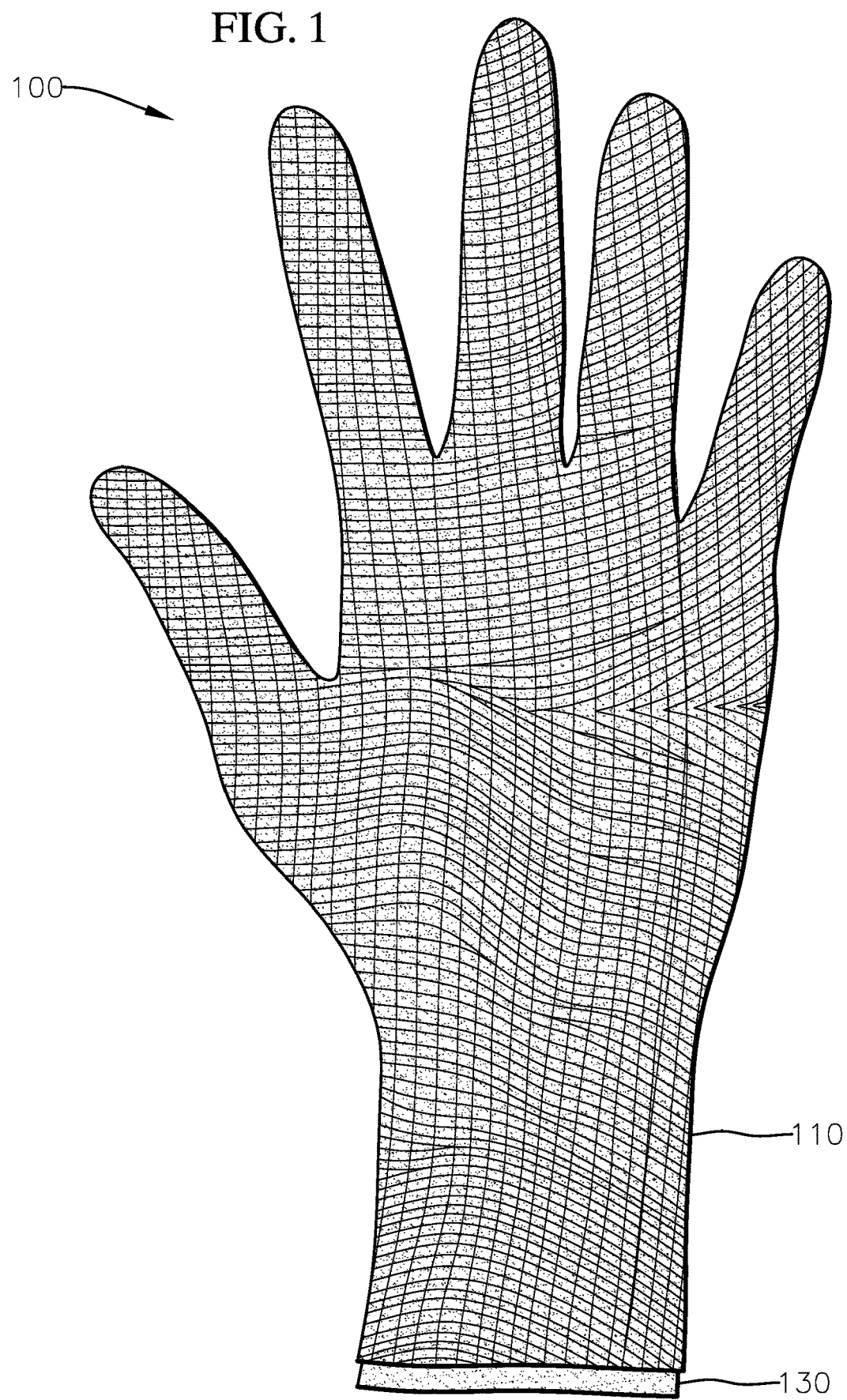
FIG. 1 is a frontal view of a palmar side of a friction creating surgical glove, according to some aspects of the present disclosure.

Features of the inventive concept and methods of accomplishing the same may be understood more readily by reference to the following detailed description of embodiments and the accompanying drawings. The inventive concept may, however, be embodied in many different forms and should not be construed as being limited to the embodiments set forth herein. Rather, these embodiments are provided as examples so that this disclosure will be thorough and complete, and will fully convey the aspects and features of the present invention to those skilled in the art. Accordingly, processes, elements, and techniques that are not necessary to those having ordinary skill in the art for a complete understanding of the aspects and features of the present invention may not be described. Unless otherwise noted, like reference numerals denote like elements throughout the attached drawings and the written description, and thus, descriptions thereof will not be repeated. In the drawings, the relative sizes of elements, layers, and regions may be exaggerated for clarity.

It will be understood that, although the terms "first," "second," "third," etc., may be used herein to describe various elements, components, regions, layers and/or sections, these elements, components, regions, layers and/or sections should not be limited by these terms. These terms are used to distinguish one element, component, region, layer or section from another element, component, region, layer, or section. Thus, a first element, component, region, layer, or section described below could be termed a second element, component, region, layer, or section, without departing from the spirit and scope of the present invention.

Spatially relative terms, such as "beneath," "below," "lower," "under," "above," "upper," and the like, may be used herein for ease of explanation to describe one element or feature's relationship to another element(s) or feature(s) as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly.

It will be understood that when an element or layer is referred to as being "on," "connected to," or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

The terminology used herein is for the purpose of describing particular embodiments only and is not intended to be limiting of the present invention. As used herein, the singular forms "a," "an," and "the" are intended to include the plural forms as well, unless the context clearly indicates otherwise. It will be further understood that the terms "comprises," "comprising," "includes," and "including," when used in this specification, specify the presence of the stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list.

As used herein, the term "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present invention refers to "one or more embodiments of the present invention." As used herein, the terms "use," "using," and "used" may be considered synonymous with the terms "utilize," "utilizing," and "utilized," respectively. Also, the term "exemplary" is intended to refer to an example or illustration.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

I. Friction Creating Surgical Glove

One or more embodiments according to the present disclosure will now be described. As described previously, the proper use personal protective equipment (PPE) within the medical field is generally required and in nearly all medical settings the use of protective gloves is commonplace. Protective gloves may have different constructions depending on the setting where they will be used, but the most common type of protective gloves are thin elastomeric gloves (often referred to as surgical gloves) that are made from latex, nitrile, vinyl, polyethylene, or other elastomeric materials. These gloves form a protective barrier between the medical practitioner and the patient to help prevent cross-contamination with bacteria, viruses, fungi, and other contaminants/pathogens. These are especially important during procedures where there are open cuts into the body, such as during a surgical operation, or during procedures where there may be a significant amount of bodily fluids involved such as delivering a baby.

During such procedures, when the surgical gloves are exposed to bodily fluids like blood, the exterior surface of the gloves can become slippery and thereby reduce the amount of grip provided to the glove wearer. In some circumstances, the glove wearer may be able to compensate for this by applying an increased amount of force to his or her grip, but in many instances this will not be possible. For example, during a surgical operation where delicate internal organs have to be held and/or moved by a medical practitioner, adding increased grip pressure may compromise the safety of the organs. Likewise, while delivering a baby, a practitioner may need to be able to securely grip a wet newborn without applying too much grip pressure to the baby.

To provide increased friction/grip, some gloves have attempted to use a texturized surface on the palmar and/or finger surfaces. However, these structures, such as bumps, ridges, negative/concave indentations, and suction cups, all have drawbacks. In particular, these structures may limit or diminish such gloves' tactile attributes, e.g., the ability feel the textures in surfaces through the glove and to finely control items held while wearing the glove. Adding surface structures to a glove may also increase the cost of production of such gloves.

Aspects of embodiments of the present disclosure may thus be directed to a friction creating surgical glove that may increase the amount of friction available on the surface of the glove when exposed to fluids. Aspects of embodiments of the individual components of the friction creating surgical glove of the present disclosure will be described in more detail below. Further understanding of the individual components, and their use in combination, may be had by reference to the accompanying figures described herein.

FIG. 1 is a frontal view of a palmar side of a friction creating surgical glove 100, according to some aspects of the present disclosure. As will be discussed below in more detail, in some embodiments, the friction creating surgical glove 100 of the present disclosure may include a cotton mesh superficial glove 110 and an elastomeric inner glove 130. In some other embodiments, the elastomeric inner glove 130 may be omitted.

As will be appreciated by one skilled in the art, the cotton mesh superficial glove 110 and the elastomeric inner glove 130 are, as depicted, generally configured to snugly fit around the hands of a wearer, with the cotton mesh superficial glove 110, in some embodiments, being configured to be pulled over or coupled to the exterior of the elastomeric inner glove 130.

A. Cotton Mesh Superficial Glove

Figure 2:
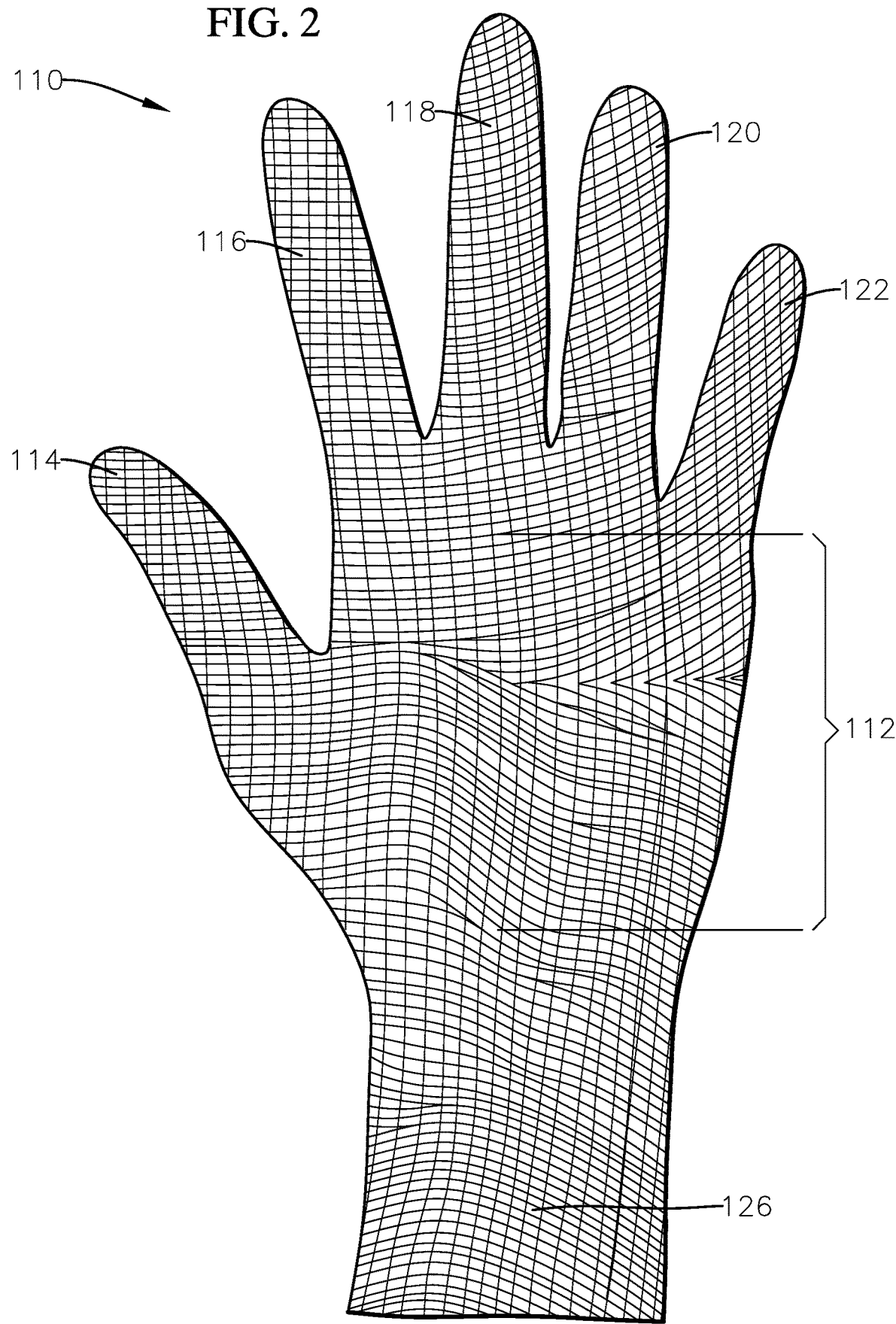
FIG. 2 is a frontal view of a palmar side of a cotton mesh superficial glove, according to some aspects of the present disclosure.

Aspects of embodiments of the present disclosure may be directed to a cotton mesh superficial glove. Further understanding of the cotton mesh superficial glove may be found by reference to FIG. 2 in view of the description provided below. FIG. 2 is a frontal view of a palmar side of a cotton mesh superficial glove 110, according to some aspects of the present disclosure.

As depicted in FIG. 2, the cotton mesh superficial glove 110 of the present disclosure may, in some embodiments include various portions corresponding to different parts of a wearer's hand. As a non-limiting example, this may include a palmar portion 112, a backhand portion (113 of FIG. 7), a thumb portion 114, a first finger portion 116, a second finger portion 118, a third finger portion 120, and a fourth finger portion 122. In some embodiments these portions may be formed in a unitary or continuous layer. In some other embodiments, the cotton mesh superficial glove 110 may also include a cuff portion 126.

The use of cotton mesh to form the cotton mesh superficial glove 110, i.e., the outermost layer of the friction creating surgical glove 100 of the present disclosure, may, in some embodiments, provide increased friction during use while the friction creating surgical glove 100 is wet or damp. Cotton has material properties that may make it well suited to this application, such as but not limited to its elasticity, texture, absorbency, and strength. As a non-limiting example, the property of cotton fibers to provide increased coefficients of friction on a surface while wet or damp with fluid makes it well suited for use within the cotton mesh superficial glove 110 of the present disclosure. As will be appreciated by one skilled in the art, there may be a number of reasons why wetted cotton fibers create an increased coefficient of friction in comparison to dry cotton fibers, and there may be other fibers that have similar absorbency and friction-increasing properties when wet. These may include natural or synthetic fibers that have similar properties to those of cotton, such as fibers produced from bamboo or hemp. Such fibers, or blends of such fibers are within the scope of the present disclosure and the use of "cotton" may be used to encompass such fibers unless otherwise specified.

There are also commercial properties for natural cotton that make it a material well-suited for use within the context of the present disclosure, such as the commercial availability of sterilized (or sterilizable), medical grade, natural cellulose fiber, cotton. This material is frequently utilized in the medical field and its availability may help to reduce production costs and difficulties.

The cotton mesh superficial glove 110 may, in some embodiments, be constructed from or otherwise incorporate sterilized, medical grade, natural cellulose fiber, cotton. Other grades and/or types of cotton fiber as would be known by one skilled in the art to be suitable for this purpose may be used within the scope of the present disclosure. In some embodiments, there may be reductions in manufacturing cost by using types and grades of cotton fiber that are commonly used throughout the medical industry.

Some embodiments of the cotton mesh superficial glove 110 may use cotton fibers formed into a mesh having a 24×20 mesh size. As will be appreciated by one skilled in the art, the mesh size may be varied within the scope of the present disclosure. There may be, in some embodiments, a tradeoff between using a finer mesh size and the effect that the cotton mesh superficial glove 110 has on the tactile attributes of the friction creating surgical glove of the present disclosure. In some embodiments, there may be different versions of the cotton mesh superficial glove 110 having different mesh sizes that may be interchangeably used to provide a user with different levels of increased friction. As a non-limiting example, a smaller mesh size may be used when bleeding is expected to be high, and then a larger mesh size may be used after the bleeding has been slowed to allow for increased tactile response during the delicate portions of an operation. Any suitable mesh size as would be known to one skilled in the art to be suitable for this purpose may be used within the scope of the present disclosure, and gap sizes in the mesh may range from about 1.00 mm to 1.00 cm may be used.

In some embodiments, the cotton mesh superficial glove 110 may include a cotton material that has been treated to have hemostatic properties. Non-limiting examples of such treatments include surface coatings containing hemostatic agents such as oxidized cellulose, the inclusion of oxidized nitrocellulose fibers within the cotton mesh, and dippable treatments using a solution containing one or more hemostatic agents that may be absorbed into the cotton mesh. As will be appreciated by one skilled in the art, any hemostatic agent or treatment known to be suitable for surgical purposes may be used within the scope of the present disclosure.

Some embodiments of the cotton mesh superficial glove 110 may include portions of the cotton mesh that contain oxidized cellulose fibers to provide hemostatic properties to the cotton mesh. The oxidized cellulose fibers may be derived from cotton fibers or regenerated cellulose fibers. In some embodiments, regenerated cellulose fibers may be used to produce the oxidized cellulose fibers as the regenerated cellulose provides increased structural and chemical consistency compared to cellulose fibers derived from cotton.

In some embodiments, a portion of the fibers that make up the cotton mesh may include a blend of fibers including oxidized cellulose fibers. As will be appreciated by one skilled in the art, the ratio of fibers in the blend may be adjusted to meet varying user needs.

In some embodiments, there may only be hemostatic material or hemostatic treatments of portions of the cotton mesh superficial glove 110. The use of hemostatic agents on the cotton mesh superficial glove 110 may, in some embodiments, help to stop bleeding in areas that are otherwise difficult to reach with anything but a fingertip. As a non-limiting example, some embodiments of the cotton mesh superficial glove 110 may include hemostatic materials or treatments on the finger portions, e.g., the first finger portion 116, of the cotton mesh superficial glove 110.

The cotton mesh superficial glove 110 may, in some embodiments, be formed with about the same shape as a traditional elastomeric surgical glove. That is, it may be formed to closely follow the surface of a wearer's hand and have sizing for the various portions of the cotton mesh superficial glove 110 similar in size to the corresponding portions of the wearer's hand. However, variations in size and proportion are contemplated within the scope of the present disclosure. Thus, although the cotton mesh superficial glove 110 may be sized as a one-size-fits-all glove, it may also be made in various sizes similar to those commonly used for traditional elastomeric surgical gloves. These sizes may, in some embodiments, use a Small, Medium, Large, Extra Large range of size options.

In some embodiments, the cotton mesh superficial glove 110 may include an increased number of cotton fibers, or an increased thickness of the cotton mesh, along the palmar portion 112. Increased grip along the palmar portion 112 may be beneficial in some use cases, and the addition of an extra thick layer of the cotton mesh at the palmar portion 112 may, in some embodiments, be used to increase grip while avoiding adding extra mesh along the finger portions that may otherwise hinder the ability of the wearer to feel fine textures while wearing the friction creating surgical glove 110.

In some other embodiments, not shown, the palmar portion 112 may include one or more gauze pads to aid in fluid absorption and increasing the friction of the palmar portion 112 while wet.

1. Customizable Embodiments

The understanding of one or more embodiments of a customizable friction creating surgical glove 200 may be had by viewing FIGS. 3-4 in connection with the description provided below.

Figure 3:
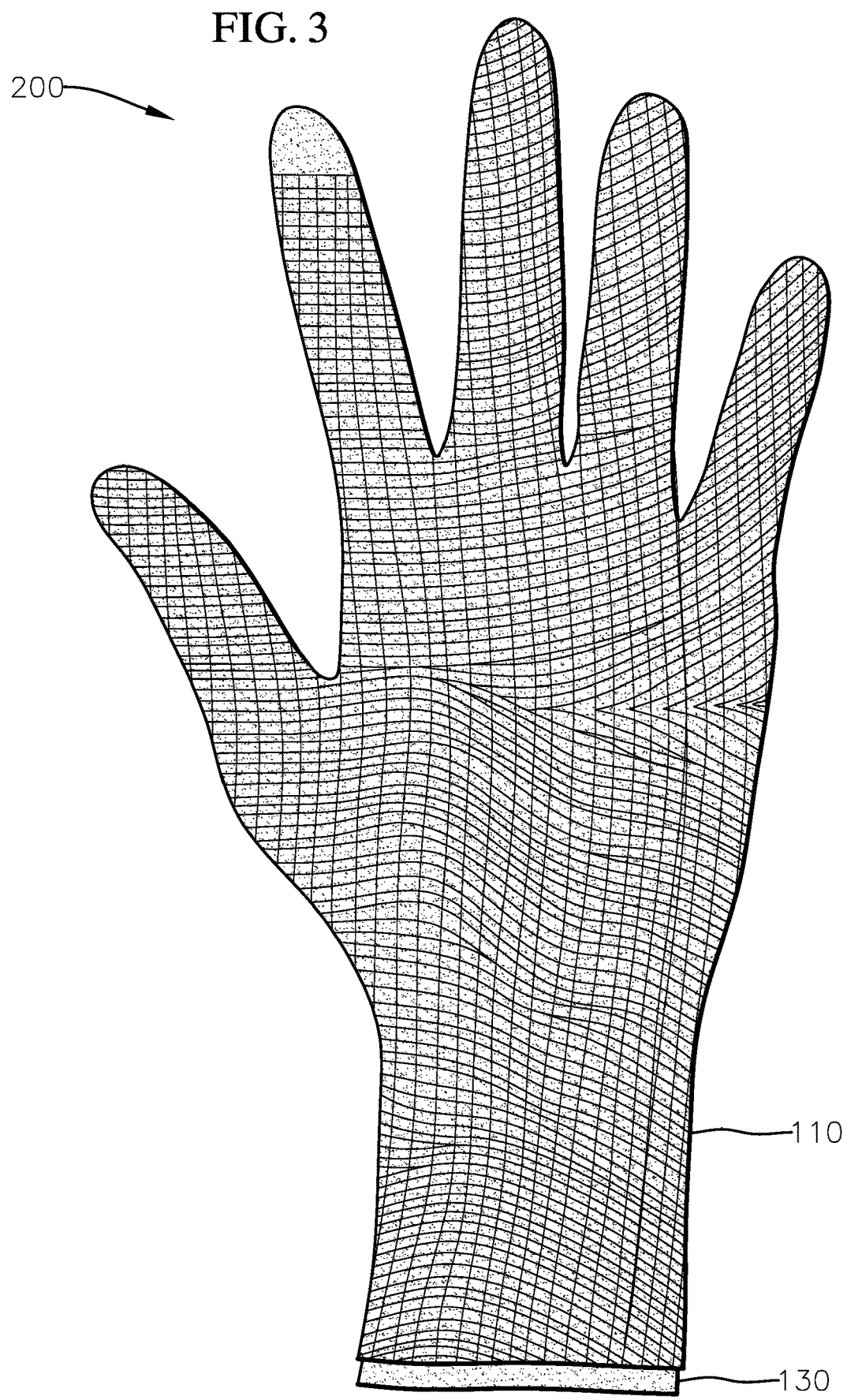
FIG. 3 is a frontal view of a customizable friction creating surgical glove having a fingertip portion of a cotton mesh superficial glove removed, according to some aspects of the present disclosure.
Figure 4:
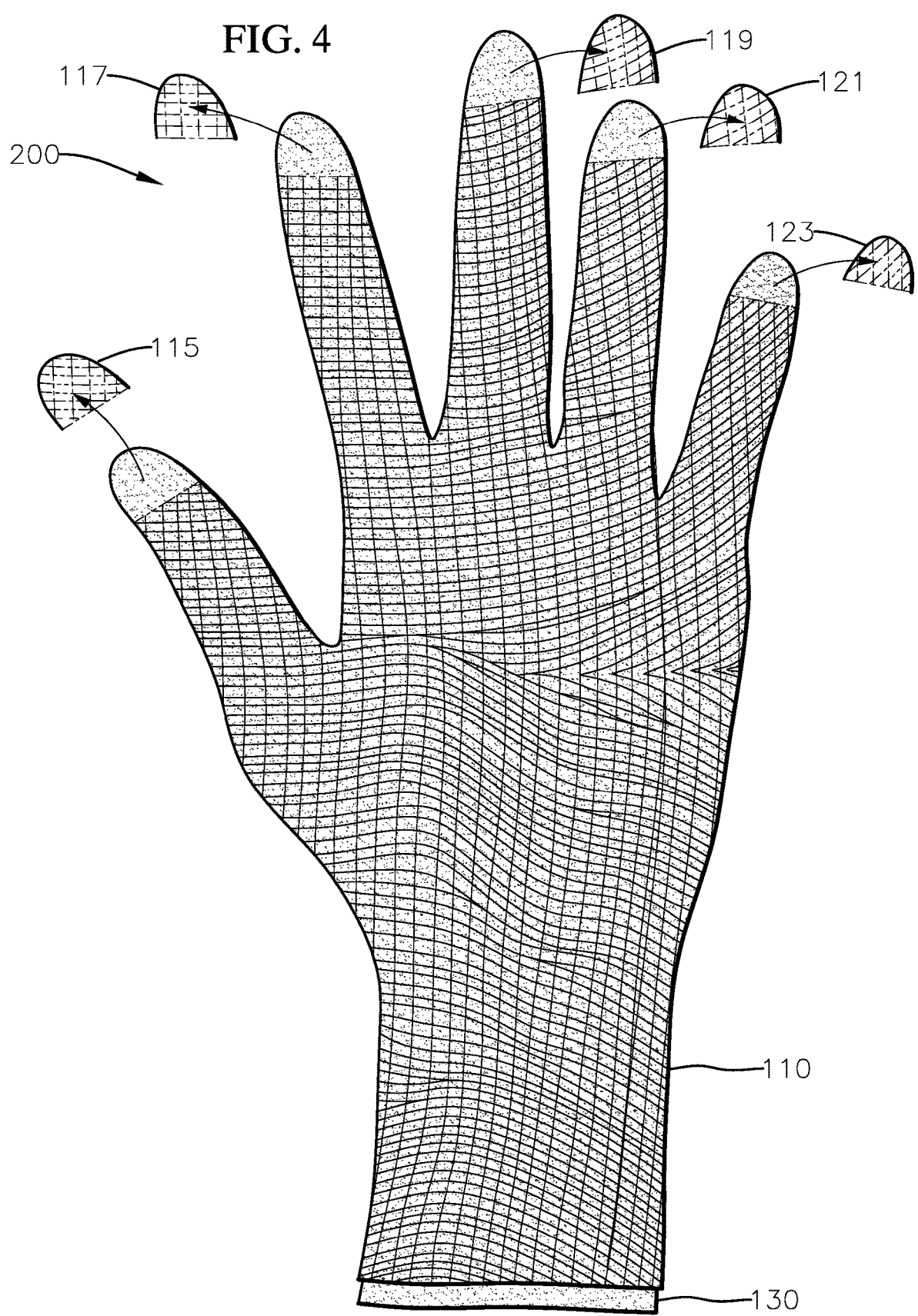
FIG. 4 is a frontal view of a customizable friction creating surgical glove having all fingertip portions of a cotton mesh superficial glove separated from the cotton mesh superficial glove, according to some aspects of the present disclosure.

FIG. 3 is a frontal view of a customizable friction creating surgical glove having a fingertip portion of a cotton mesh superficial glove removed, according to some aspects of the present disclosure. As described above, the friction creating surgical gloves of the present disclosure may include a cotton mesh superficial glove 110 that may be used with or without an underlying glove layer, such as the elastomeric inner glove described in detail below. Glove layers may be necessary to create the sterile boundaries that help to prevent infection and contamination of open cuts to the body of a patient during a procedure and prevent exposure to infection/contagions for the medical practitioner. However, these intervening layers may also reduce the tactile response, i.e., the ability to feel fine textures and make precise movements, available to the medical practitioner during a procedure. As such, some embodiments of the cotton mesh superficial glove 110 of the present disclosure may be configured to have separable portions that may be selectively removed from the remaining portions of the cotton mesh superficial glove 110 to allow for the use of a customizable friction creating surgical glove 200.

Some embodiments of the customizable friction creating superficial glove 200 may be configured to allow for the selective removal/severing of one or more fingertip portions from one or more of the finger portions of the cotton mesh superficial glove 110, i.e., the first finger portion 116, the second finger portion 118, the third finger portion 120, and the fourth finger portion 122. Some other embodiments may be configured to also allow for the selective removal/severing of a tip portion of the thumb portion 114. These fingertip portions can be seen in FIG. 4. FIG. 4 is a frontal view of a customizable friction creating surgical glove having all fingertip portions of a cotton mesh superficial glove 110 separated from the cotton mesh superficial glove 110, according to some aspects of the present disclosure. As depicted, these "tip" or "fingertip" portions may include a thumb tip portion 115, a first fingertip portion 117, a second fingertip portion 119, a third fingertip portion 121, and a fourth fingertip portion 123.

As will be appreciated by one skilled in the art, any combination of the thumb tip portion 115 and the fingertip portions (117, 119, 121, and 123) may be selectively removed/severed by a wearer to meet his or her specific needs. As a non-limiting example, a wearer may select and sever the first fingertip portion 117 and the second fingertip portion 119 while leaving the remainder of the cotton mesh superficial glove 110 intact in order to decrease the potential loss of tactile response for those fingers that may be necessary for palpating or feeling textures during a procedure but otherwise keeping as much cotton mesh in place as possible to ensure increase friction and grip.

As another non-limiting example, a wearer may select and sever the first fingertip portion 117 from the first finger portion 116 (i.e., the index finger portion), to preserve as much feel for fine textures on that fingertip while wearing the customizable friction creating surgical glove 200 of the present disclosure while still increasing the friction on the palmar portion 112 and remaining fingertip portions (119, 121, and 123).

This may, in such embodiments, allow for the wearer to customize the areas of the cotton mesh superficial glove that most effect the tactile attributes of the glove during use. Such embodiments may also allow for a wearer to prepare differently customized cotton mesh superficial gloves 110 that may be swapped out and worn over the elastomeric inner glove 130 as needed during a medical procedure.

In some embodiments, the fingertip portions may be severed or otherwise separated from the finger portions of the cotton mesh superficial glove 110 using shears, scalpels, or any other cutting instrument. However, any suitable instrument for severing/removing portions of the cotton mesh superficial glove 110 may be used within the scope of the present disclosure.

B. Elastomeric Inner Glove

Aspects of embodiments of the present disclosure may be directed to an elastomeric inner glove (130 of FIG. 1) that may be used with the cotton mesh superficial glove 110. The cotton mesh superficial glove 110 described above may provide increased friction while wet, but it is not a continuous physical barrier to prevent the spread of bacteria, virus, pathogens, and other contaminants between medical practitioner and patient. As such, in some embodiments, an elastomeric inner glove 130 may be used in conjunction with the cotton mesh superficial glove 110 to provide such a barrier.

In some embodiments, the elastomeric inner glove 130, may be made of latex, nitrile, vinyl, polyethylene, or other elastomeric materials. In some other embodiments, the elastomeric inner glove 130 may be made in various sizes to facilitate a comfortable fit for different hand sizes.

In some embodiments, the cotton mesh superficial glove 110 may be used in connection with the elastomeric inner glove 130 by stretching or otherwise fitting the cotton mesh superficial glove 110 over the elastomeric inner glove 130. Such embodiments may be referred to as "pull-on" embodiments. For some such embodiments, during use, a used cotton mesh superficial glove 110 may be removed and replaced with a new cotton mesh superficial glove 110 as needed due to wear or oversaturation with fluids.

As described above, a customizable friction creating surgical glove 200 may, in some embodiments, allow for the selective removal of one or more portions of the cotton mesh superficial glove 110 while keeping an intact elastomeric inner glove 130 to maintain a physical boundary between the wearer and a patient or the environment. In some such embodiments, the cotton mesh superficial layer 110 may be customized before being pulled over the elastomeric inner glove 130. In some other embodiments, the cotton mesh superficial glove 110 may be customized after being placed over the elastomeric inner glove 130. In still other embodiments, a wearer may differently customize several cotton mesh superficial gloves 110 to be swapped out during the course of a procedure to provide the wearer with different levels of friction and tactile response as needed during the procedure.

In some embodiments, the cotton mesh superficial glove 110 may be integrated or otherwise bonded with the elastomeric inner glove 130 such that it is not intended to be removed. This may, in some embodiments, include bonding the cotton mesh superficial glove 110 along a portion of the elastomeric inner glove 130. This bonding may be performed using glues, adhesives, tapes, or any other physical structure as would be known to be suitable for this purpose by one skilled in the art. Likewise, as will be appreciated by one skilled in the art, any suitable method for decoupling or otherwise removing the cotton mesh superficial glove 110 from the elastomeric inner glove 130 may be used within the scope of the present disclosure.

C. Gauze Pocket and Radio-Opaque Liner

Aspects of embodiments of the present disclosure may be directed to a gauze pocket that may be configured to house or otherwise retain a radio-opaque liner and/or an RFID tag. Further understanding of the features may be had by reference to FIGS. 5 and 6 alongside the detailed description provided below.

Figure 5:
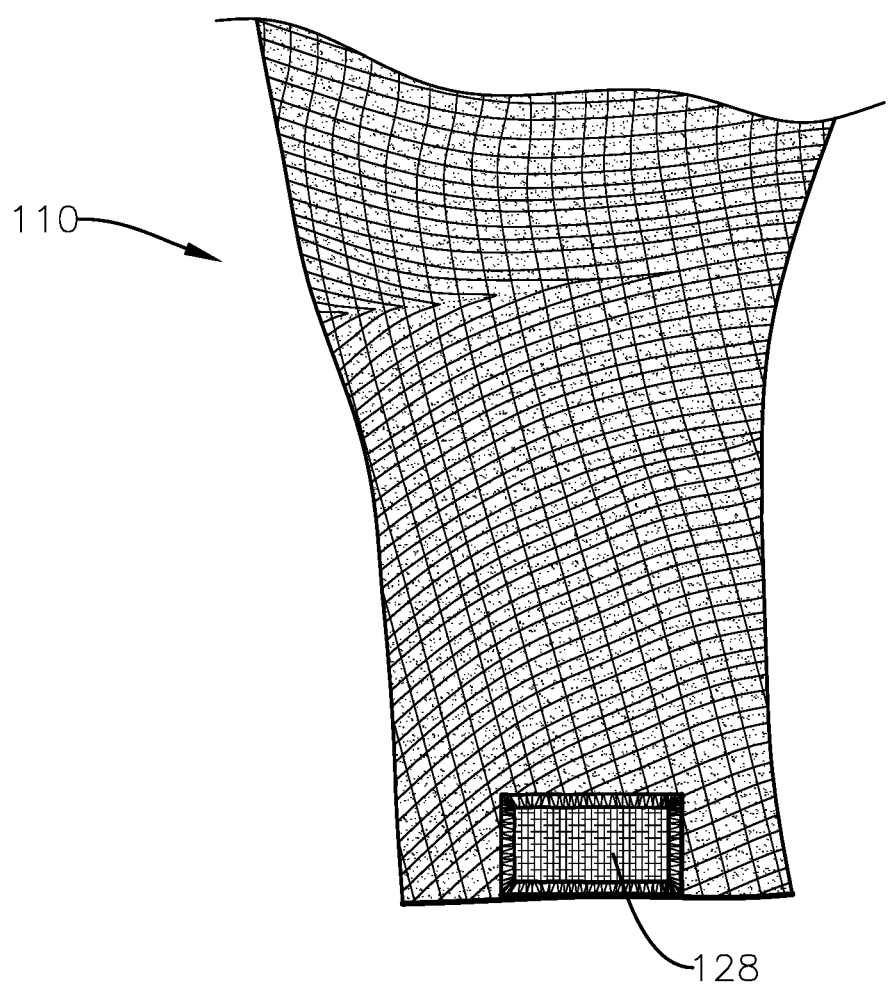
FIG. 5 is a frontal view of a cuff portion of a cotton mesh superficial glove coupled to a gauze pocket, according to some aspects of the present disclosure.

FIG. 5 is a frontal view of a cuff portion 126 of a cotton mesh superficial glove 110 coupled to a gauze pocket 128, according to some aspects of the present disclosure.

The gauze pocket 128 may, in some embodiments, be constructed from sterile medical grade surgical gauze. However, as will be appreciated by one skilled in the art, any suitable gauze capable of being sterilized without losing form or function may be used within the scope of the present disclosure. In some embodiments, the gauze pocket 128 may be constructed of non-gauze materials or fabrics. In still other embodiments, the gauze pocket 128 may include multiple layers of gauze or other materials that may increase the thickness and durability of the gauze pocket 128.

In some embodiments, the gauze pocket 128 may be coupled to the cotton mesh superficial glove 110. In some other embodiments the gauze pocket 128 may be sewn together with the cotton mesh superficial glove 110. However, any suitable method known to one skilled in the art for coupling or otherwise securing the gauze pocket 128 to the cotton mesh superficial glove 110 may be used within the scope of the present disclosure. This may include, but is not limited to, glues, thermal bonding, adhesive tapes, and other physical structures suited for binding to a mesh such as Velcro® or other hook-and-loop type structures.

Figure 6:
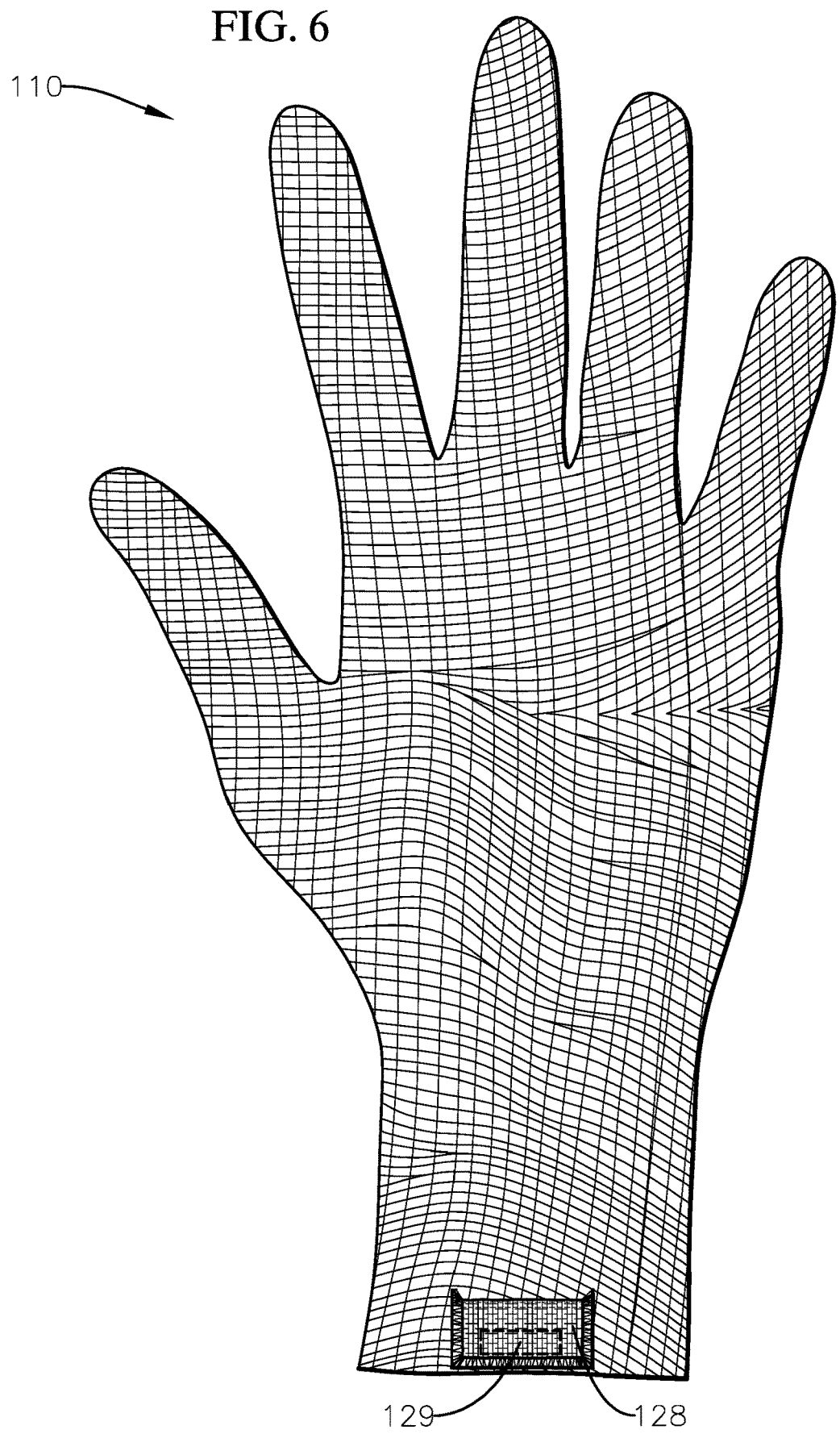
FIG. 6 is a frontal view of a palmar side of a cotton mesh superficial glove coupled to a gauze pocket housing a radio-opaque liner, according to some aspects of the present disclosure.

The gauze pocket may, in some embodiments, be configured to house a radio-opaque liner or an RFID tag 129 as seen in FIG. 6. FIG. 6 is a frontal view of a palmar side of a cotton mesh superficial glove coupled to a gauze pocket housing a radio-opaque liner, according to some aspects of the present disclosure. The radio-opaque liner or RFID tag 129 may be used to assist in tracking/locating the friction creating surgical glove of the present disclosure during and after use. In some embodiments, the radio-opaque liner or RFID tag 129 may be constructed from a material that contains at least 55% barium sulfate. However, as will be appreciated by one skilled in the art, any suitable material may be used within the scope of the present disclosure. In some other embodiments the gauze pocket 128 may be configured to house or otherwise retain an RFID tag that may be integrated within a computerized inventory control system. The use of such an RFID tag may allow for computerized inventory control and recording of supplies used during a procedure.

In some embodiments, the gauze pocket 128 may be configured to have an opening to facilitate the placement and removal of liner or tags from within the gauze pocket 128. In some other embodiments, the gauze pocket 128 may be constructed from a gauze that may bee seen through. Such embodiments may provide a wearer with an easy way to visually check the friction creating surgical glove 100 to ensure that a liner or tag has been placed within the gauze pocket 128 prior to use.

1. Radio-Opaque Strip

Figure 7:
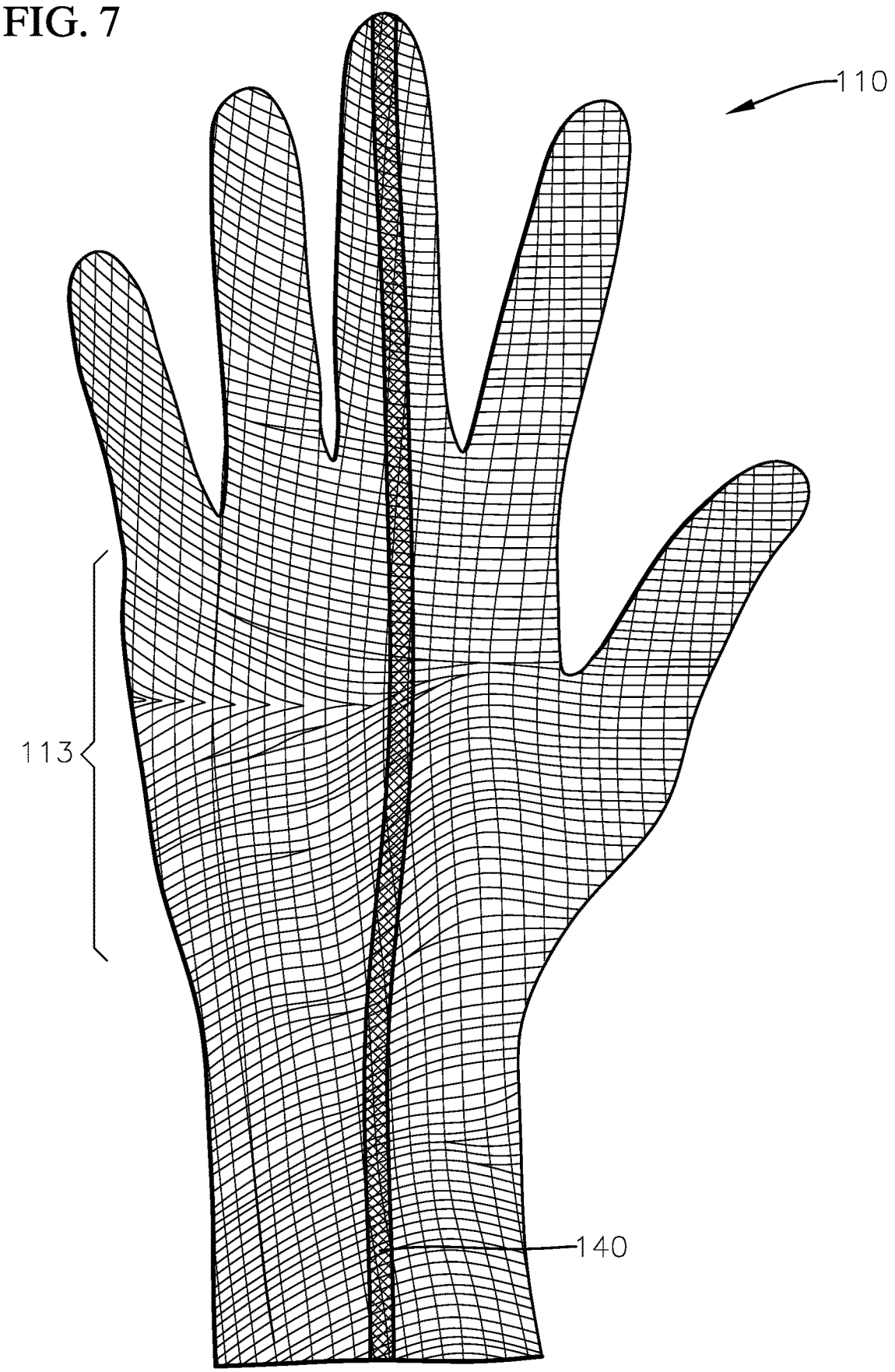
FIG. 7 is a frontal view of a backhand side of a cotton mesh superficial glove having a sewn-in radio-opaque liner, according to some aspects of the present disclosure.

The use of a radio-opaque strip 140 allows for some embodiments of the friction creating surgical glove 100 of the present disclosure to be easily discoverable using an X-ray following a procedure if there are any unaccounted for items after the procedure has been completed. In some embodiments, the cotton mesh superficial glove 110 may be coupled to a radio-opaque strip 140 as shown in FIG. 7. FIG. 7 is a frontal view of a backhand side of a cotton mesh superficial glove 110 having a sewn-in radio-opaque liner 140, according to some aspects of the present disclosure. The radio-opaque strip 140 may, in some embodiments, be sewn into the cotton mesh superficial glove 110 to provide a reliable coupling of the radio-opaque strip 140 to the cotton mesh superficial glove 110.

The placement of the radio-opaque strip 140 may, in some embodiments, be on a backhand portion 113 of the cotton mesh superficial glove 110 as depicted in FIG. 7. However, as will be appreciated by one skilled in the art, the placement of the radio-opaque strip 140 may be varied to meet different wearer needs. Generally, the radio-opaque strip 140 may be constructed of any materials that are opaque to radio wave frequency light, including but not limited to materials that contain at least 55% barium sulfate. As will be appreciated by one skilled in the art, any radio-opaque material or combination of materials as would be known to be suitable for this purpose may be used. In some embodiments, the radio-opaque strip 140 may be constructed from a wound or woven material. In some such embodiments, the radio-opaque strip 140 may be flexible. The use of a flexible radio-opaque strip 140 may help to reduce any restrictions on the hand movement of a wearer during use.

In some other embodiments, not depicted, the radio-opaque strip 140 may be located along the cuff portions 126 of the cotton mesh superficial glove 110. In some such embodiments, the radio-opaque strip 140 may be placed to encircle or partially encircle the wrist of a wearer during use and thereby avoid limiting the tactile response available to the wearer during use.

As will be appreciated by one skilled in the art, embodiments of the present disclosure may include both the gauze pocket 128 configured to house an RFID tag 129 and the radio-opaque strip 140.

D. Method for Use/Customization

Aspects of the present disclosure are directed to methods for donning and/or customizing embodiments of the customizable friction creating surgical glove 200.

In some embodiments, the method may include donning, by a user/wearer, an elastomeric inner glove. The method may also, in some embodiments, include selecting, by the user/wearer, one or more fingertip portions (115, 117, 119, 121, and 123 of FIG. 4) of a cotton mesh superficial glove 110 for removal and then severing the selected one or more fingertip portions of the cotton mesh superficial glove 110. This process may be referred to as customization. The method may then, in some embodiments, proceed to stretching, by the user/wearer, the cotton mesh superficial glove 110 over the elastomeric inner glove 130 thereby forming the customizable friction creating surgical glove 200.

In some other embodiments, both the elastomeric inner glove 130 and the cotton mesh superficial glove 110 may be placed onto the hand of a wearer before customization. However, this may increase the risk to the wearer for inadvertent cuts to the elastomeric inner glove and/or the hand of the wearer.

As discussed above, the customization of the cotton mesh superficial glove 110 may allow for a wearer to meet different needs for grip and/or tactile response for different procedures or different parts of a single procedure. The customization process may also include preparing multiple customized cotton mesh superficial gloves 110 that may be swapped out for use during a procedure as needed. This may, in some embodiments, allow for the elastomeric inner glove 130 to remain in place during the entire procedure while the customized cotton mesh superficial gloves 110 are used and replaced. This may help to preserve an intact physical barrier between the hand of a wearer and a patient during the procedure and reduce the risk of cross-contamination.

It will be understood that embodiments described herein should be considered in a descriptive sense only and not for purposes of limitation. Descriptions of features or aspects within each exemplary embodiment should typically be considered as available for other similar features or aspects in other embodiments.

While one or more exemplary embodiments have been described with reference to the figures, it will be understood by those of ordinary skill in the art that various changes in form and details may be made therein without departing from the spirit and scope as defined by the following claim. It should be noted that although examples of the invention are set forth herein, the claims, and the full scope of any equivalents, are what define the metes and bounds of the invention.

What is claimed is:

1. A friction creating surgical glove system, comprising:
    a unitary cotton mesh superficial glove, comprising:
        a palmar portion;
        a thumb portion;
        a first finger portion;
        a second finger portion;
        a third finger portion; and
        a fourth finger portion; and a gauze pocket coupled to the unitary cotton mesh superficial glove configured to house a radio-opaque liner.

2. The friction creating glove system of claim 1, further comprising:
an elastomeric inner glove configured to couple to the unitary cotton mesh superficial glove.

3. The friction creating glove system of claim 1, wherein the unitary cotton mesh superficial glove further comprises sterilized medical grade, natural cellulose fiber, cotton.

4. The friction creating glove system of claim 3, wherein the sterilized medical grade, natural cellulose fiber, cotton has a 24×20 mesh size.

5. The friction creating glove system of claim 1, wherein the unitary cotton mesh superficial glove further comprises:
a backhand portion.

6. The friction creating glove system of claim 5, wherein the unitary cotton mesh superficial glove forms an outer layer including the palmar portion, the backhand portion, the thumb portion, the first finger portion, the second finger portion, the third finger portion, and the fourth finger portion.

7. The friction creating glove system of claim 1, wherein each of the first finger portion, the second finger portion, the third finger portion, and the fourth finger portion are configured to have removeable fingertip portions.

8. The friction creating glove system of claim 7, wherein the thumb portion is configured to have a removeable thumb tip portion.

9. The friction creating glove system of claim 1, further comprising:
a sewn-in radio-opaque strip along the backhand portion of the unitary superficial cotton mesh glove.

10. A friction creating surgical glove apparatus, comprising:
a unitary cotton mesh superficial glove, comprising:
a palmar portion;
a thumb portion; and
a finger portion;
a gauze pocket coupled to the unitary cotton mesh superficial glove configured to house a radio-opaque liner; and
an elastomeric inner glove.

11. The friction creating surgical glove apparatus of claim 10, wherein the unitary cotton mesh superficial glove further comprises sterilized medical grade, natural cellulose fiber, cotton.

12. The friction creating surgical glove apparatus of claim 11, wherein the sterilized medical grade, natural cellulose fiber, cotton has a 24×20 mesh size.

13. The friction creating surgical glove apparatus of claim 10, wherein the finger portion comprises a distal tip that is severable from a proximal portion of the finger portion.

14. The friction creating surgical glove apparatus of claim 10, herein the thumb portion comprises a distal thumb tip that is severable from a proximal thumb portion of the thumb portion.

15. The friction creating surgical glove apparatus of claim 10, wherein the radio-opaque liner comprises an RFID tag.

16. The friction creating surgical glove apparatus of claim 10, wherein the radio-opaque liner comprises a liner material containing at least 55% barium sulfate.

17. The friction creating surgical glove apparatus of claim 10, wherein the unitary cotton mesh superficial glove is bonded to the elastomeric inner glove along a binding portion of the elastomeric inner glove.

18. A method for donning a friction creating surgical glove, comprising:
donning, by a user, an elastomeric inner glove;
selecting, by the user, one or more fingertip portions of a unitary cotton mesh superficial glove for removal;
severing, by the user, the selected one or more fingertip portions of the unitary cotton mesh superficial glove; and
stretching, by the user, the unitary cotton mesh superficial glove over the elastomeric inner glove thereby forming the friction creating surgical glove.

19. The method for donning a friction creating surgical glove of claim 18, wherein the unitary cotton mesh superficial glove comprises sterilized medical grade, natural cellulose fiber, cotton.

20. The method for donning a friction creating surgical glove of claim 18, further comprising:
presenting, by the user, an RFID tag coupled to the friction creating surgical glove to an RF receiver.

* * * * *